United States Patent [19]

Marcus

[11] 3,966,333
[45] June 29, 1976

[54] MAGNETIC STIRRER NOISE CANCELLATION SYSTEM

[75] Inventor: Byron E. Marcus, Columbia, Md.

[73] Assignee: Baxter Laboratories, Inc., Deerfield, Ill.

[22] Filed: Feb. 3, 1975

[21] Appl. No.: 546,676

[52] U.S. Cl. .......................... 356/229; 259/DIG. 46; 356/222; 356/246
[51] Int. Cl.² .......................................... G01J 1/10
[58] Field of Search .......... 356/229, 222, 173, 246; 259/DIG. 46, 1 R; 324/34 R

[56] References Cited
UNITED STATES PATENTS

| 3,622,128 | 11/1971 | Geiser | 259/DIG. 46 |
| 3,730,488 | 5/1973 | Gardner, Jr. | 259/DIG. 46 |
| 3,784,170 | 1/1974 | Petersen et al. | 259/DIG. 46 |
| 3,882,716 | 5/1975 | Beiman | 259/DIG. 46 |

Primary Examiner—John K. Corbin
Assistant Examiner—Stewart Levy
Attorney, Agent, or Firm—Herman L. Gordon; Richard G. Kinney

[57] ABSTRACT

A system for compensating for magnetic disturbances caused by the rotating stirrer magnet of a photometer sample cuvette on the photomultiplier tube of the photometer. To obtain the required compensation, a companion similar magnet is located coplanar with and adjacent to the main stirrer magnet and is counter-rotated synchronously with the main magnet in opposite magnetic phase therewith. The two counter-rotating magnets are physically located symmetrically with respect to the photomultiplier tube so that their magnetic effects on the electron flow of the photomultiplier tube cancel each other out. The companion magnet may be the stirrer magnet associated with a reference cuvette mounted in side-by-side relation to the sample cuvette. The counter-rotating magnets may be gearingly coupled together and may be mounted coaxially with respective ejection plungers associated with the cuvettes.

14 Claims, 9 Drawing Figures

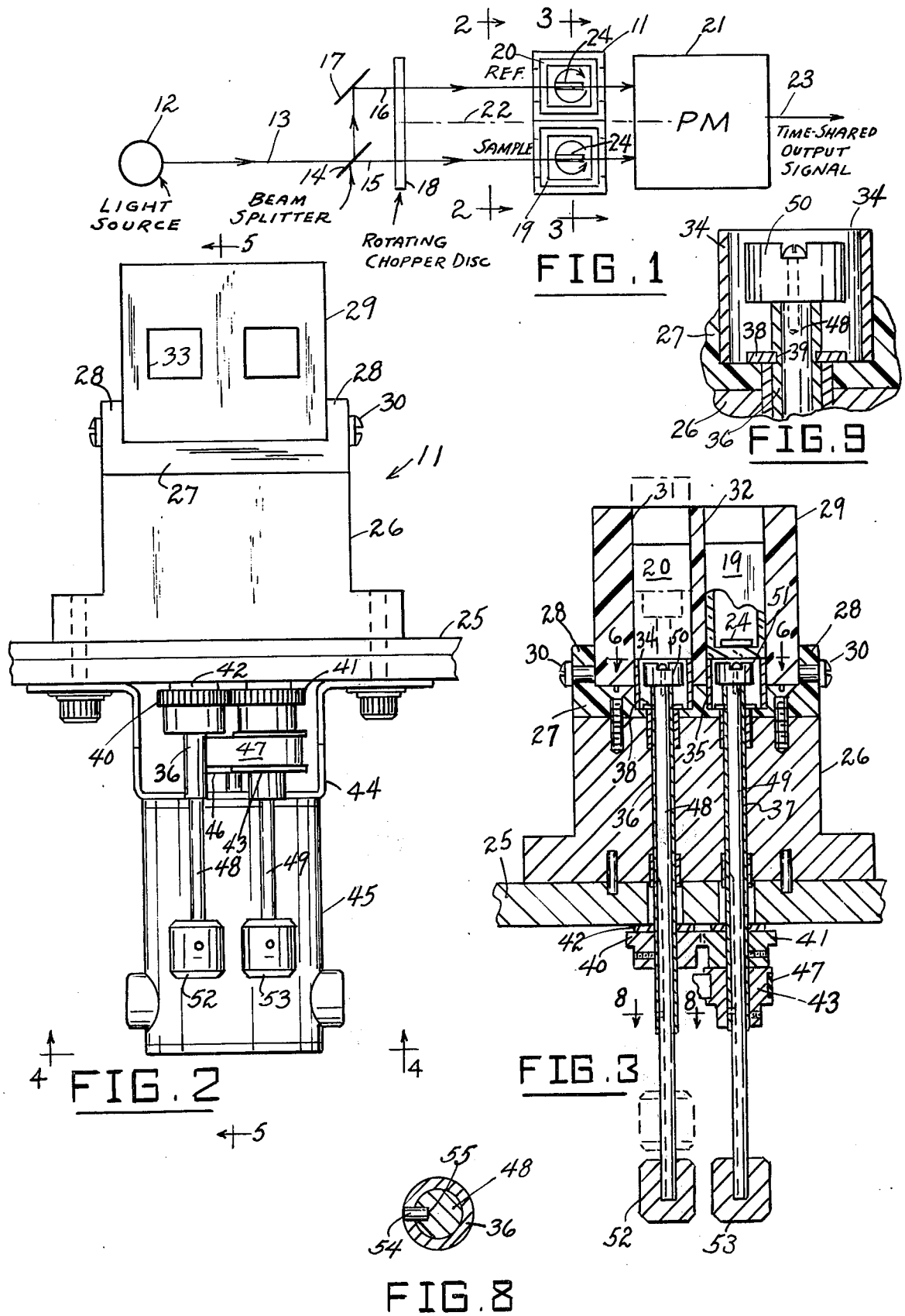

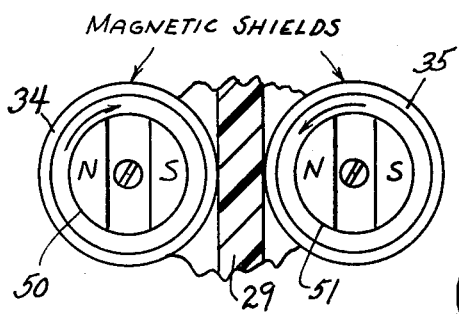
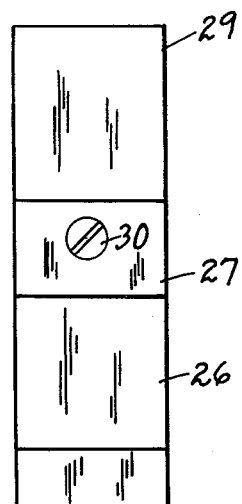
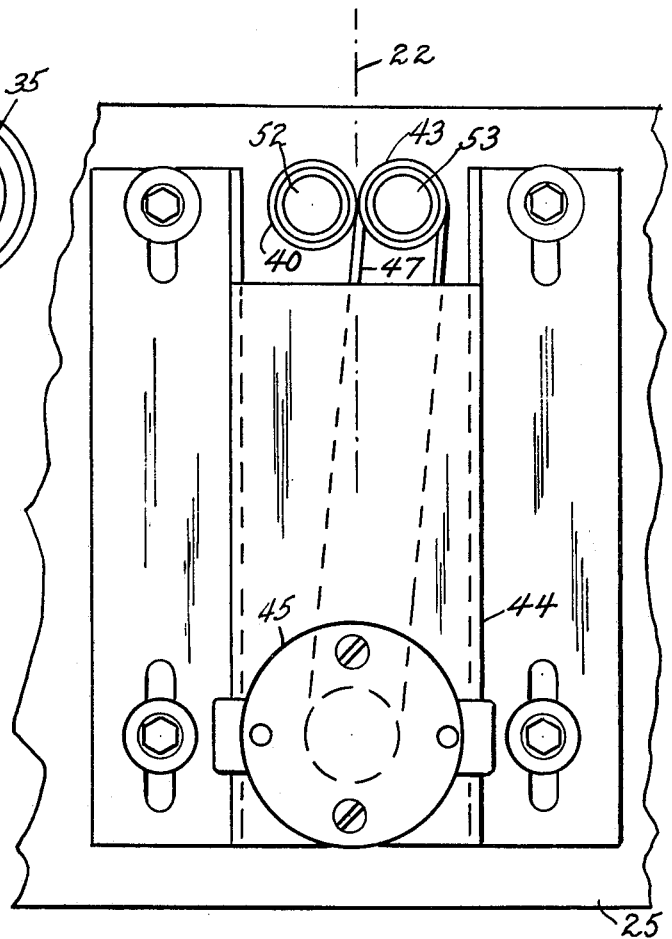
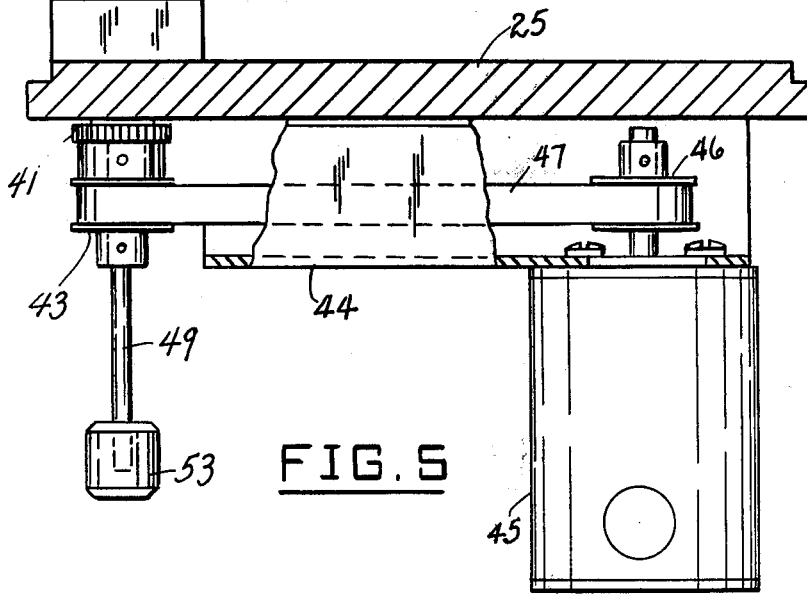
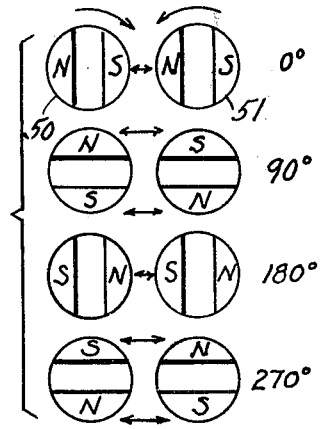

MAGNETIC STIRRER NOISE CANCELLATION SYSTEM

This invention relates to noise-compensation systems for photometers, and more particularly to systems for compensating for or minimizing magnetic disturbances or magnetic noise effects on the photomultiplier tube of a photometer.

A main object of the invention is to provide a novel and improved compensation system for minimizing the magnetic disturbance effect of a magnetic stirrer employed with the sample cuvette of a photometer of the type employing a photomultiplier tube as a photosensitive element.

A further object of the invention is to provide an improved method and means for substantially eliminating the magnetic disturbances produced in the signal output of the photomultiplier tube of a spectrophotometer, or similar photometer, by the rotation of the magnetic stirrer drive means employed with the sample cuvette of the instrument, the method and means requiring simple apparatus and providing effective compensation for the rotating magnetic field of the stirrer drive means.

A still further object of the invention is to provide an improved system for greatly reducing or substantially eliminating magnetic disturbances in the photomultiplier tube of a photometer caused by the action of a rotating magnetic stirrer drive magnet associated with the sample cuvette of the photometer, the system involving relatively inexpensive components, being easy to install, and efficiently suppressing the magnetic disturbances by balancing the field of the magnetic stirrer drive magnet against an equal and opposite compensating field.

A still further object of the invention is to provide a compact, efficient and inexpensive magnetic stirrer field-cancelling system for a photometer photomultiplier tube in a spectrophotometer or similar instrument, wherein a sample cuvette and a reference cuvette are employed, each being provided with stirrer means, the system employing a configuration wherein at the photomultiplier tube the respective stirrer magnetic fields are in opposing relation and substantially balance each other out in a way to minimize magnetic noise effects in the photomultiplier output signal.

Further objects and advantages of the invention will become apparent from the following description and claims, and from the accompanying drawings, wherein:

FIG. 1 is a schematic diagram of the optical system of a typical double beam photometer employing a sample cuvette and a reference cuvette having respective magnetic stirrers and employing a magnetic stirrer field-cancelling system according to the present invention.

FIG. 2 is an enlarged elevational view of a typical magnetic stirrer assembly which may be employed in the photometer of FIG. 1, taken substantially on the line 2—2 of FIG. 1.

FIG. 3 is a vertical cross-sectional view taken through the typical stirrer assembly substantially on the line 3—3 of FIG. 1.

FIG. 4 is a bottom plan view taken substantially on the line 4—4 of FIG. 2.

FIG. 5 is a vertical cross-sectional view taken substantially on the line 5—5 of FIG. 2.

FIG. 6 is an enlarged fragmentary horizontal cross-sectional view taken substantially on the line 6—6 of FIG. 3.

FIG. 7 is a diagram illustrating the positions of the stirrer magnets of FIG. 6 at progressive stages in the cycle of rotation of said magnets.

FIG. 8 is an enlarged horizontal cross-sectional view taken substantially on the line 8—8 of FIG. 3.

FIG. 9 is an enlargement of a fragmentary portion of FIG. 3 showing the detailed rotational supporting structure for one of the stirrer magnet drive tubes.

Referring to the drawings, FIG. 1 schematically illustrates the conventional optical system of a double-beam photometer employing a cuvette-supporting assembly, designated generally at 11, provided with magnetic noise compensation means according to the present invention. The typical photometer of FIG. 1 comprises a suitable light source 12 which generates a light beam 13 directed by conventional means to a beam splitter 14, such as a half-silvered mirror, which thereby provides a main beam 15 and a reference beam 16, which is reflected by a plane mirror 17 so as to travel parallel to main beam 15, as shown. Beams 15 and 16 are alternately blocked by a conventional rotating chopper disc 18 as they travel toward the cuvette assembly 11 and pass through a sample cuvette 19 and a reference cuvette 20. The emergent beams alternately impinge on a photomultiplier tube 21 located on the axis 22, said cuvettes 19 and 20 being located symmetrically on opposite sides of said axis 22. The alternating beams passing through cuvettes 19 and 20 thus cause photomultiplier tube 21 to generate a time-shared output signal at its output 23, which is handled in a conventional manner to derive information, such as data based on a comparison of the optical effects of the sample material in cuvette 19 and the reference material in cuvette 20.

It is necessary and desirable to agitate the material in the cuvettes, and therefore suitable stirrer means is employed. Conventionally, the stirrer means comprises a rotatable free magnetic stirrer rod 24 disposed in the bottom of each cuvette, the stirrer rod being driven by a suitable rotating stirrer magnet axially mounted below each cuvette and being magnetically coupled to the stirrer rod therein.

In prior arrangements, the magnetic fields of the rotating stirrer magnets produced substantial noise disturbances in the output signal of the photomultiplier tube because of the more-or-less random reactions between the magnetic fields and the flow of electrons between the cathode and anode elements of the tube. In such prior arrangements no attempt was made to control said magnetic fields in a manner to reduce or minimize these noise effects. The present invention aims to minimize and substantially eliminate such magnetic noise effects by balancing the stray magnetic field of a rotating stirrer magnet against the corresponding stray field generated by a similar and symmetrically disposed synchronously counter-rotating magnet. In the typical case herein presented, the counter-rotating compensation magnet is that associated with the comparison cuvette. The two rotating magnets are mounted symmetrically with respect to the associated photomultiplier tube and are phased so that their nearest adjacent poles are always of opposite polarity, the magnets being synchronously driven in opposite directions. The phasing is such that the distances between the adjacent opposite-polarity poles are held to a minimum and vary between maximum at parallelism of the magnets and minimum at alignment of the magnets. As above mentioned, the rotating magnets are oppositely phased relative to the photomultiplier tube. Thus, the stray flux from the respective rotating magnets has equal and opposite effects on the flow of electrons in the photomultiplier tube, so that these effects substantially cancel each other.

Referring to the typical cuvette-supporting assembly 11 shown in FIGS. 2 to 5, the assembly comprises a base plate 25 on which is secured an upstanding block 26. Fastened on the top of mounting block 26 is an insulator block 27 having upstanding side ribs 28, 28, defining a seat therebetween which receives a double cuvette holder 29, secured between ribs 28, 28 by fastening screws 30. Holder 29 is formed with side-by-side square vertical bores 31, 32 shaped to slidably receive the respective transparent square cuvettes 20, 19, as shown in FIG. 3. The holder 29 is provided with light-transmitting apertures or windows 33 for the light beams 15, 16.

Block 27 is formed beneath bores 31, 32 with recesses in which are mounted respective upstanding cylindrical magnetic shield members 34, 35 of suitable high-permeability material, also forming supporting rests for the cuvettes 20, 19, as shown in FIG. 3. Journalled vertically in block members 27, 26 coaxially with shields 34, 35 and extending downwardly through plate 25 are respective drive tubes 36, 37. The tubes are rotatably supported by snap collar rings 38 engaged in peripheral grooves 39 formed in the top portions of the tubes, as shown in FIG. 9. Secured on the tubes 36, 37 below plate 25 are intermeshed identical gears 40, 41, with spacer washers 42 provided between the gears and plate 25. A drive pulley 43 is secured on the lower end of tube 37.

A channel-shaped bracket 44 is adjustably secured to the bottom of plate 25, and secured to the web of said bracket is a depending drive motor 45. Pulley 43 is drivingly coupled by a belt 47 to a pulley 46 secured on the shaft of motor 45. Respective magnet shafts 48, 49 are slidably keyed in tubes 36 and 37, and secured on the top ends of said shafts are respective generally cylindrically stirrer drive magnets 50, 51, which normally rest on the top ends of tubes 36, 37. The shafts 48, 49 extend a substantial distance below the lower ends of the tubes, as shown in FIG. 3, and are provided at their bottom ends with cuvette ejection knobs 52, 53.

As shown in FIG. 3, the magnets 50, 51 are normally supported slightly below the bottom walls of the cuvettes. The cuvettes may be elevated above the top plane of the holder 29 for removal by pushing upwardly on the knobs 52, 53. For example, cuvette 20 may be elevated to the upwardly extended dotted view position thereof of FIG. 3 by pushing on the knob 52.

The shafts 48, 49 may be slidably keyed to their drive tubes 36, 37 in any suitable manner. For example, as shown in FIG. 8, the drive tubes may be provided with inwardly projecting pins 54 slidably engaging in longitudinal keyways 55 formed in the shafts.

In operation, motor 45 drives tubes 36, 37 synchronously in opposite directions because of the gearing cooperation of the meshed gears 40, 41. This similarly drives the magnets 50, 51 in opposite directions, and likewise drives the magnetic stirrer rods 24 in the cuvettes in opposite directions, following the rotation of the magnets 50, 51.

As shown in FIGS. 6 and 7, the permanent magnets 50, 51 are phased so that the south pole of magnet 50 comes directly opposite the north pole of magnet 51 in a position such as that shown in FIG. 6. This is the 0° position shown in FIG. 7. There is thus a minimum-length air path between the adjacent south-north poles above the magnetic shields 34, 35. This low-reluctance path attracts a large amount of the stray magnetic flux produced by the magnets. The remainder of the stray flux from the respective magnets reaches the photomultiplier tube with equal and opposite effects on the electron flow therein, as above explained, whereby said residual stray flux produces negligible signal noise effects in the tube. The residual stray flux field changes symmetrically as the magnets counter-rotate toward the 90° position shown in FIG. 7. Upon reaching this position practically all of the stray magnetic flux is still concentrated in the still relatively short air gaps between the adjacent north-south and south-north poles of the magnets. The 180° position provides a condition similar to that of the 0° position; the 270° position provides a reversed, but equally effective condition similar to that of the 90° position.

Some variation from exact alignment of the magnets is possible within the spirit of the present invention, but the abovedescribed specific arrangement provides optimum reduction of magnetic stirrer noise in the photomultiplier signal. Driving the stirrer magnets synchronously in the same direction rather than in opposite directions has been found to be less satisfactory in that it tends to produce a pulsating magnetic field, causing corresponding noise pulses in the photomultiplier output signal.

In general, the alignment or phasing of the counter-rotating stirrer magnets according to the present invention should be such as to cause oppositely poled magnet portions to move towards each other at most portions of the cycle so as to maintain a substantial stray field susceptance condition (relatively low average reluctance) in the region between and closely adjacent to the spaces immediately above the magnets. This absorbs a considerable portion of the stray field and tends to minimize the remaining stray field strength, namely, that of the stray field pulsations reaching the photomultiplier tube; thus these pulsations are at relatively low amplitudes when they cancel each other.

Any suitable means may be employed, within the spirit of the present invention, to couple the magnets 50, 51 together for synchronous counter-rotation. For example, the magnet drive tubes 36, 37 may be coupled by sprocket wheels and a sprocket chain, or other equivalent positive-coupling means, instead of being coupled by the meshing gears 40, 41.

It is also to be noted that in single-cuvette systems, the desired compensation for magnetic disturbances associated with the cuvette magnetic stirrer may be obtained by merely employing a companion counter-rotating magnet similarly arranged and driven in the same manner as above described, without using a second cuvette.

Additionally it is to be noted that within the spirit of the present invention, the sample stirrer magnet and the companion magnet need not necessarily be arranged symmetrically with respect to the photomultiplier tube. The same compensation effect can be achieved by employing a suitable less powerful synchronously counter-rotating companion magnet positioned closer to the photomultiplier tube and coupled to the sample stirrer magnet by suitable gearing or other positive drive means. Also, it is possible to employ suitable circuit means which senses the stirrer magnet stray field at the photomultiplier tube and generates a compensation signal which may be employed to balance out the stirrer magnet stray field noise.

While a specific embodiment of a system for compensating for magnetic disturbances caused by a typical cuvette magnetic stirrer assembly has been disclosed in the foregoing description, it will be understood that various modifications within the spirit of the invention may occur to those skilled in the art. Therefore it is intended that no limitations be placed on the invention except as defined by the scope of the appended claims.

1. In an optical photometer device of the type employing a photosensitive electronic valve device, a sample cuvette, means to direct a light beam to the cuvette and to direct a resultant emergent beam to the electronic valve device, whereby to generate an electrical signal, and magnetic stirrer means including a movable stirrer magnet adjacent said cuvette and electronic valve device and a magnetic driven element in the cuvette, magnetic noise compensation means comprising a movable companion magnet adjacent said stirrer magnet and electronic valve device, means to support the magnetic so that they can be repetitively cyclically moved, the respective magnets having north and south poles, means intercoupling the magnets to move them synchronously in opposite senses, the magnets being mounted on the supporting means so that poles of opposite polarity of the respective magnets move alternately toward and away from each other as the magnets are cyclically moved in said opposite senses, and means to drive said stirrer magnet and companion magnet, whereby their magnetic fields interact in a manner to minimize the magnetic field acting on the electronic valve device.

2. The optical photometer device of claim 1, and wherein the magnets are rotatably mounted and are arranged so that they can be rotated to aligned positions with their inwardly adjacent poles of opposite polarity.

3. The optical photometer device of claim 1, and wherein the means intercoupling the magnets includes intermeshing gears drivingly connected to the respective magnets.

4. The optical photometer device of claim 1, and wherein the stirrer magnet and the companion magnet are located substantially symmetrically with respect to the electronic valve device.

5. The optical photometer device of claim 1, and wherein the means intercoupling said stirrer magnet and companion magnet includes means to rotate said magnets simultaneously in opposite directions.

6. The optical photometer device of claim 1, and wherein the cuvette is provided with positioning means in which the cuvette is slidably receivable and in which the cuvette can be elevated to an upwardly extended position, and wherein the stirrer magnet underlies the cuvette and is provided with vertically movable support shaft means, and means to at times elevate said support shaft means so as to raise said cuvette to said upwardly extended position.

7. The optical photometer device of claim 6, and wherein the means to drive the stirrer magnet includes a rotatable drive tube receiving said support shaft means, and means slidably keying said support shaft means to said drive tube.

8. The optical photometer device of claim 7, and wherein the means intercoupling the magnets includes intermeshing gear means drivingly connected to the drive tube and the companion magnet.

9. The optical photometer device of claim 1, and wherein the photometer device is provided with a cuvette holder formed to receive said sample cuvette and a reference cuvette in side-by-side relation and wherein said companion magnet is employed as a stirrer drive magnet for said reference cuvette.

10. The optical photometer device of claim 9, and wherein the sample cuvette stirrer magnet and the companion magnet are arranged to respectively underlie the sample cuvette and the reference cuvette and are provided with respective vertically movable support shafts and with vertical rotatable drive tubes receiving and slidably keyed to said support shafts.

11. The optical photometer device of claim 10, and wherein said intercoupling means comprises intermeshing gears on said drive tubes for rotating the magnets synchronously and in opposite directions.

12. The optical photometer device of claim 11, and wherein the magnets are located substantially symmetrically relative to the electronic valve device.

13. In an instrument including a photosensitive electronic valve device and a nearby magnetically cyclically-driven device having a cyclically-moving drive magnet, means to compensate for the pulsating magnetic field effects produced on the electronic valve device by the drive magnet comprising means to generate an auxiliary cyclical magnetic signal opposite in phase to that produced by the cyclically moving drive magnet, and means to support said signal-generating means in a position such that its field strength at the electronic valve device substantially balances the field strength of the magnetic signal produced by said cyclically-moving drive magnet.

14. The instrument of claim 13, and wherein said means to generate the auxiliary cyclical magnetic signal comprises an auxiliary magnet mounted adjacent the electronic valve device, and means drivingly coupling said auxiliary magnet to said drive magnet to move it cyclically in a sense opposite to that of the drive magnet.

* * * * *

UNITED STATES PATENT AND TRADEMARK OFFICE
CERTIFICATE OF CORRECTION

PATENT NO. : 3,966,333
DATED : June 29, 1976
INVENTOR(S) : Byron E. Marcus

It is certified that error appears in the above-identified patent and that said Letters Patent are hereby corrected as shown below:

Column 5, line 26, delete "magnetic" and insert therefor
-- magnets -- .

Signed and Sealed this

Twenty-seventh Day of June 1978

[SEAL]

Attest:

RUTH C. MASON
Attesting Officer

DONALD W. BANNER
Commissioner of Patents and Trademarks